US011107015B2

(12) United States Patent
Chen et al.

(10) Patent No.: US 11,107,015 B2
(45) Date of Patent: Aug. 31, 2021

(54) INFORMATION EXCHANGE SYSTEM AND METHOD

(71) Applicant: DrFirst.com, Inc., Rockville, MD (US)

(72) Inventors: James F. Chen, Naples, FL (US); Peter N. Kaufman, Potomac, MD (US); Glenn Cameron Deemer, Mesa, AZ (US); Eric Rosenfeld, Frederick, MD (US); Brandon Anthony Brylawski, Bethesda, MD (US); Jesus Cardozo Ramirez, Tempe, AZ (US); Prasith Govin, Washington, DC (US); Plamen Gurov, Germantown, MD (US); ChihSheng Tsai, Oak Hill, VA (US)

(73) Assignee: DrFirst.com, Inc., Rockville, MD (US)

( * ) Notice: Subject to any disclaimer, the term of this patent is extended or adjusted under 35 U.S.C. 154(b) by 875 days.

(21) Appl. No.: 15/583,184

(22) Filed: May 1, 2017

(65) Prior Publication Data
US 2017/0235890 A1    Aug. 17, 2017

Related U.S. Application Data

(63) Continuation of application No. 13/890,068, filed on May 8, 2013, now abandoned.
(Continued)

(51) Int. Cl.
*G06Q 10/06* (2012.01)
*G06Q 10/00* (2012.01)
(Continued)

(52) U.S. Cl.
CPC .......... *G06Q 10/06* (2013.01); *G06Q 10/00* (2013.01); *G16H 10/60* (2018.01); *G16H 40/67* (2018.01);
(Continued)

(58) Field of Classification Search
CPC .. G06F 19/328; G06F 19/3418; G06F 19/321; G06F 16/211; G06F 16/258;
(Continued)

(56) References Cited

U.S. PATENT DOCUMENTS 5,845,255 A    12/1998  Mayaud
5,950,630 A    9/1999   Portwood et al.
(Continued)

FOREIGN PATENT DOCUMENTS

JP    2001-357131 A    12/2001
JP    3974800 B2       9/2007

OTHER PUBLICATIONS

Atre, S. (2007). Relational view of XML for the semantic web (Order No. MR37247). Available from ProQuest Dissertations and Theses Professional (Year: 2007).*
(Continued)

*Primary Examiner* — Joseph D Burgess
(74) *Attorney, Agent, or Firm* — Brake Hughes Bellermann LLP (57) ABSTRACT

A health information exchange (HIE) system and related methods for sharing patient medical data among a plurality of users. In one embodiment, the HIE system includes a processor executing a software application and one or more databases. Medical data may be downloaded by a first user to the system in a source file format. The system converts and stores the medical data in a data record such as an object having a different type of data structure. Upon receiving a request from a second user for the medical data in a specified destination file format, the system retrieves and converts the object containing the medical data into the specified destination file format, and sends the destination file to the second user. The source and destination file formats may be
(Continued)

the same or different. In one embodiment, users may access and communicate with the HIE system via the Internet.

20 Claims, 5 Drawing Sheets

Related U.S. Application Data (60) Provisional application No. 61/644,182, filed on May 8, 2012.

(51) Int. Cl.
  *G16H 40/67* (2018.01)
  *G16H 10/60* (2018.01)
  *G06F 16/21* (2019.01)
  *G06F 16/178* (2019.01)
  *G06F 16/23* (2019.01)

(52) U.S. Cl.
  CPC ........ *G06F 16/1794* (2019.01); *G06F 16/211* (2019.01); *G06F 16/2365* (2019.01)

(58) Field of Classification Search
  CPC ........ G06F 16/986; G06F 19/00; G06F 16/86; G06F 21/6218; G06F 16/2264; G06F 16/283; G06Q 50/24; G06Q 50/22; G16H 10/60; G16H 10/65; G16H 30/20; G16H 30/40; G16H 15/00; G16H 80/00; G16H 50/70
  See application file for complete search history.

(56) References Cited

U.S. PATENT DOCUMENTS

| | | | |
|---|---|---|---|
| 5,966,702 A | 10/1999 | Fresko et al. | |
| 6,112,182 A | 8/2000 | Akers et al. | |
| 6,125,447 A | 9/2000 | Gong | |
| 6,240,394 B1 | 5/2001 | Uecker et al. | |
| 6,578,003 B1 | 6/2003 | Camarda et al. | |
| 6,859,780 B1 | 2/2005 | Cunningham | |
| 7,046,691 B1* | 5/2006 | Kadyk | H04L 12/66 370/466 |
| 7,519,540 B2 | 4/2009 | Mayaud | |
| 7,606,723 B2 | 10/2009 | Mayaud | |
| 7,679,520 B2 | 3/2010 | Zerhusen et al. | |
| 7,729,927 B2 | 6/2010 | Cunningham | |
| 7,797,731 B2 | 9/2010 | Bhagavatula et al. | |
| 7,925,531 B1 | 4/2011 | Cunningham et al. | |
| 7,945,461 B2 | 5/2011 | Sekura | |
| 7,996,260 B1 | 8/2011 | Cunningham et al. | |
| 8,010,379 B2 | 8/2011 | Tamblyn et al. | |
| 8,055,542 B1 | 11/2011 | Cunningham et al. | |
| 8,108,226 B2 | 1/2012 | Barrett et al. | |
| 8,121,868 B1 | 2/2012 | Grady et al. | |
| 8,255,241 B2 | 8/2012 | Cafer | |
| 8,301,466 B2 | 10/2012 | Lorsch | |
| 2001/0027403 A1 | 10/2001 | Peterson et al. | |
| 2001/0032124 A1 | 10/2001 | Savage et al. | |
| 2001/0037216 A1 | 11/2001 | Oscar et al. | |
| 2002/0032582 A1 | 3/2002 | Feeney, Jr. et al. | |
| 2003/0009367 A1 | 1/2003 | Morrison | |
| 2003/0050799 A1 | 3/2003 | Jay et al. | |
| 2003/0074234 A1 | 4/2003 | Stasny | |
| 2003/0088771 A1 | 5/2003 | Merchen | |
| 2003/0177033 A1 | 9/2003 | Park et al. | |
| 2003/0212577 A1 | 11/2003 | Nichtberger | |
| 2004/0181428 A1 | 9/2004 | Fotsch et al. | |
| 2005/0125257 A1 | 6/2005 | Ziegele et al. | |
| 2005/0159977 A1 | 7/2005 | Green et al. | |
| 2005/0171817 A1 | 8/2005 | Sachdev et al. | |
| 2006/0059017 A1 | 3/2006 | Louik et al. | |
| 2006/0136197 A1* | 6/2006 | Oon | G06F 40/186 704/9 |
| 2006/0178910 A1 | 8/2006 | Eisenberger et al. | |
| 2006/0235726 A1 | 10/2006 | Paraison et al. | |
| 2006/0247968 A1 | 11/2006 | Kadry | |
| 2006/0282447 A1* | 12/2006 | Hollebeek | G06F 16/86 |
| 2007/0067186 A1 | 3/2007 | Brenner et al. | |
| 2007/0078680 A1 | 4/2007 | Wennberg | |
| 2007/0172424 A1 | 7/2007 | Roser | |
| 2007/0174092 A1 | 7/2007 | Lara et al. | |
| 2007/0219827 A1 | 9/2007 | Green | |
| 2007/0260491 A1 | 11/2007 | Palmer et al. | |
| 2007/0294112 A1 | 12/2007 | Settimi | |
| 2008/0077430 A1 | 3/2008 | Singer et al. | |
| 2008/0104104 A1* | 5/2008 | Nolan | G06Q 10/06 |
| 2008/0126276 A1 | 5/2008 | Williams et al. | |
| 2008/0133273 A1 | 6/2008 | Marshall | |
| 2008/0215361 A1 | 9/2008 | Nunnari et al. | |
| 2008/0228525 A1 | 9/2008 | Weickert et al. | |
| 2008/0244453 A1 | 10/2008 | Cafer | |
| 2009/0043608 A1 | 2/2009 | Nadas et al. | |
| 2009/0089392 A1 | 4/2009 | Fiedotin et al. | |
| 2009/0119129 A1 | 5/2009 | Nadas et al. | |
| 2009/0164376 A1 | 6/2009 | Guthrie | |
| 2009/0240513 A1 | 9/2009 | Angell et al. | |
| 2009/0240523 A1 | 9/2009 | Friedlander et al. | |
| 2009/0240702 A1 | 9/2009 | Bluth | |
| 2009/0287502 A1 | 11/2009 | Roberts et al. | |
| 2009/0319291 A1 | 12/2009 | Noordvyk et al. | |
| 2009/0326977 A1 | 12/2009 | Cullen et al. | |
| 2009/0327363 A1 | 12/2009 | Cullen et al. | |
| 2010/0042440 A1 | 2/2010 | Joao | |
| 2010/0082369 A1 | 4/2010 | Prenelus et al. | |
| 2010/0114602 A1 | 5/2010 | Joao et al. | |
| 2010/0131299 A1* | 5/2010 | Hasan | G06Q 10/10 705/3 |
| 2010/0131502 A1 | 5/2010 | Fordham | |
| 2010/0153174 A1 | 6/2010 | Angell et al. | |
| 2010/0153389 A1 | 6/2010 | Angell et al. | |
| 2010/0161353 A1 | 6/2010 | Mayaud | |
| 2010/0211407 A1 | 8/2010 | Duke et al. | |
| 2010/0228567 A1 | 9/2010 | Wulf | |
| 2010/0241445 A1 | 9/2010 | Rago et al. | |
| 2011/0015978 A1 | 1/2011 | Welch, Jr. | |
| 2011/0119076 A1 | 5/2011 | Dhoble | |
| 2011/0125521 A1 | 5/2011 | Dhoble | |
| 2011/0131060 A1 | 6/2011 | Schuster et al. | |
| 2011/0173047 A1 | 7/2011 | Kelley | |
| 2011/0178813 A1 | 7/2011 | Moore | |
| 2011/0184753 A1 | 7/2011 | Tripoli | |
| 2011/0184755 A1 | 7/2011 | Yamaga et al. | |
| 2011/0184756 A1 | 7/2011 | Yamaga et al. | |
| 2011/0213622 A1 | 9/2011 | Berman | |
| 2011/0238321 A1 | 9/2011 | Slotman | |
| 2011/0238435 A1 | 9/2011 | Rapaport et al. | |
| 2011/0244919 A1 | 10/2011 | Alter et al. | |
| 2011/0257998 A1 | 10/2011 | Cinqualbre et al. | |
| 2011/0295961 A1* | 12/2011 | Wilkes | G06Q 50/24 709/206 |
| 2011/0313928 A1 | 12/2011 | Blonchek | |
| 2012/0035957 A1 | 2/2012 | Hanz et al. | |
| 2012/0101849 A1* | 4/2012 | Mathur | G06F 19/328 705/3 |
| 2012/0124640 A1* | 5/2012 | Bender | G06F 21/6218 726/1 |
| 2013/0304510 A1 | 11/2013 | Chen et al. | |

OTHER PUBLICATIONS

"Rules—2010", U.S. Department of Justice Office of Diversion Control, available online at <https://www.deadiversion.usdoj.gov/fed_regs/rules/2010/fr0331.htm>, Mar. 31, 2010 11 pages.

* cited by examiner

305
User submits original patient medical data in source file type to HIE system 310
Patient Data received by HIE Core via API 315
HIE Core sends request to Moxy Exchange Services for file conversion algorithm to convert source data file type data to a MOB 330
Core transmits and stores MOB in MOB Store database 325
HIE Core converts source data file type to MOB using supplied algorithm 320
Moxy Exchange transmits requested algorithm to HIE Core

FIG. 5

INFORMATION EXCHANGE SYSTEM AND METHOD

CROSS-REFERENCE TO RELATED APPLICATIONS

The present application is a continuation of U.S. application Ser. No. 13/890,068, filed May 8, 2013, which claims of the benefit of U.S. Provisional Application No. 61/644,182, filed May 8, 2012, which are incorporated herein by reference in their entirety.

FIELD OF THE INVENTION

The present invention generally relates to electronic health records, and more particularly to computer processor based systems and methods fur electronically storing and exchanging patient health files and medical data.

BACKGROUND OF THE INVENTION

Health Information Exchange (HIE) systems are intended to all users such as health care providers, hospitals, laboratories, and others to store, transmit, and exchange patient medical information. Hitherto, HIE systems and similar medical data repositories have generally required users to use only specific data file formats regardless of the diversity and type of medical source data (e.g. X-rays, MRIs, lab results, photographs, videos, technician notes, etc.). This has been problematic because different user IT systems often utilize different types of software and supported file formats. Accordingly, users may sometimes locate relevant patient medical data in the HIE system, but cannot view that data if the original source and user's destination file formats are not compatible. This situation has restricted the functionality of HIE systems and hampered the efficient sharing of patient medical data among those involved in providing health services to patients in a truly integrated manner which reaps the full benefits of this type of system. Allowing users to freely upload and download medical data using an HIE system regardless of file format or type restrictions can greatly increase effectiveness and patient well-being.

An improved HIE system and related methods are desired.

SUMMARY OF THE INVENTION

A Health information Exchange (HIE) system and related methods for sharing patient medical data among a plurality of users are provided which overcomes the foregoing problems. The present HIE system operates to allow the universal sharing of medical data by converting data uploaded to the HIE system by a first user regardless of the source file format or type into a destination format or type requested by a second user seeking to download and view that same medical data. The file format conversion is performed automatically by the HIE system in a manner which is invisible to the users on either by upload or download end.

In one embodiment, the HIE system generally includes a processor executing a software application and one or more databases. Medical data may be downloaded by a first user to the system in a source file format. The system converts and stores the medical data in a generic data record such as an object (Medical Object herein to connote the context of the data record object) having a different type of data structure. Upon receiving a request from a second user for the medical data in a user-specified destination file format, the system retrieves and converts the Medical Object (MOB) containing the medical data into the specified destination file format, and sends the destination file to the second user. The second user may now view the medical data regardless of the original source file format used to upload the medical data to the HIE system. The source and destination file formats may be the same or different. In one embodiment, users may access and communicate with the HIE system via the Internet, as further described herein.

There are appreciable benefits with using medical data conversions into an intermediate form such as the data record or object (MOB) in lieu of a direct one-step conversion from source to destination file formats. A prime reason for converting to as MOB and then going through a second conversion step is to retain data integrity. When one tries to convert a file directly from source A to designation H file types without going through the intermediate MOB conversion, a loss of information and poor translation is generally encountered. By introducing a middle step or MOB, one ensures that they are getting almost a double check on the medical data conversion. The MOB allows the files to all be saved in one generic form, the MOB, which has ensured that every part of the file (e.g. medical data, file attributes, properties) has been accounted for and properly captured, which avoids translation errors experienced when converting directly from source A file type to designation B file type much of the time.

In one embodiment, a computer processor implemented method for exchanging patient medical data includes: a processor of a health information exchange system receiving a first medical data file containing medical data in a first file format; the processor automatically retrieving a conversion algorithm operable to convert the first medical data file into a medical object; the processor converting the first medical data file into the medical object using the conversion algorithm to deconstruct the first file format and extract file information from the first medical data file, the extracted information then being reorganized into the medical object having a format different than the first file format; and the processor storing the medical object in a database.

In another embodiment, a computer processor implemented method for exchanging patient medical data includes: a processor of as health information exchange system receiving a source file containing medical data in a first file format; the processor converting the source file into the medical object using a file-to-object conversion algorithm, the medical object containing file information and the medical data from the source file organized in a different way than in the source file; the processor storing the medical object in a database; the processor receiving request from a user for medical data contained in the medical object; the processor retrieving the medical object from the database; the processor converting the medical object into a destination file using an object-to-file conversion algorithm, the destination file containing the requested medical data form the medical object in a second file format; and the processor sending the destination file to the user.

In one embodiment, a non-transitory computer readable storage medium encoded with instructions of a software application is provided which, when executed by a processor of a health information exchange system, cause the processor to perform steps comprising: receiving a source file containing medical data in a first file format; converting the source file into the medical object using a file-to-object conversion algorithm, the medical object containing file information and the medical data from the source file organized in a different way than in the source file; storing the medical object in a database; receiving request from a user for medical data contained in the medical object; retrieving the medical object from the database; converting the medical object into a destination file using an object-to-file conversion algorithm, the destination file containing the requested medical data form the medical object in a second file format; and sending the destination file to the user.

In another embodiment of the present invention, as health information exchange system includes a non-transitory computer readable medium encoded with a software application, a first processor executing the software application, a medical object database comprising a plurality of medical objects each containing medical data, the first processor being operable to store and retrieve medical objects from the database, and a file exchange database comprising a plurality of object-to-file and file-to-object conversion algorithms. The first processor is operable to retrieve the algorithms from the database, wherein the first processor converts medical data tiles downloaded by a user to the health information exchange system into medical objecting using the file-to-object algorithms, and wherein the first processor converts the medical objects back into medical data files when requested by a user using object-to-file algorithms.

BRIEF DESCRIPTION OF THE DRAWINGS

The features of the exemplary embodiments of the present invention will be described with reference to the following drawings where like elements are labeled similarly, and in which.

All drawings are schematic and not to scale.

DETAILED DESCRIPTION OF EMBODIMENTS

The features and benefits of the present disclosure are illustrated and described herein by reference to exemplary embodiments and are in no way intended to limit the invention, its application, or uses. This description of exemplary embodiments is intended to be read in connection with the accompanying drawings, which are to be considered part of the entire written description. Accordingly, the present disclosure expressly should not be limited to such embodiments illustrating some possible non-limiting combination of features that may exist alone or in other combinations of features; the scope of the claimed invention being defined by the claims appended hereto.

In the description of embodiments disclosed herein, any reference to direction or orientation is merely intended for convenience of description and is not intended in any way to limit the scope of the present invention. Relative terms such as "lower," "upper," "horizontal," "vertical,", "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation. Terms such as "attached," "coupled," "affixed," "connected," "interconnected," and the like refer to a relationship wherein structures are secured or attached to one another either directly or indirectly through intervening structures, as well as both movable or rigid attachments or relationships, unless expressly described otherwise. The terms "medication," "drug," and "substance" may be used interchangeably herein unless specifically noted to the contrary to define a medication prescribed by a health care provider having a potential health effect.

Computer-executable instructions/programs (e.g. code) and data described herein may be programmed into and tangibly embodied in non-transitory computer readable medium that is accessible to and retrievable by a respective processor which configures and directs the processor to perform the desired functions and processes by executing the instructions encoded in the medium. It should be noted that non-transitory "computer readable medium" as described herein may include, without limitation, any suitable volatile or non-volatile memory including random access memory (RAM) and various types thereof, read-only memory (ROM) and various types thereof, USB flash memory, and magnetic or optical data storage devices (e.g. internal/external hard disks, floppy discs, magnetic tape CD-ROM, DVD-ROM, optical disk, ZIP™ drive, Blu-ray disk, and others), which may be written to and/or read by a processor operably connected to the medium.

Features of the present invention may be implemented in software, hardware, firmware, or combinations thereof. The computer programs described herein are not limited to any particular embodiment, and may be implemented in an operating system, application program, foreground or background processes, driver, or any combination thereof. The computer programs may be executed on a single computer or server processor or multiple computer or server processors.

Processors described herein may be any computer/server central processing unit (CPU), microprocessor, micro-controller, or computational device or circuit configured for executing computer program instructions (e.g. code).

Computer-executable instructions or programs (e.g. software or code) and data described herein may be programmed into and tangibly embodied in a non-transitory computer-readable medium that is accessible to and retrievable by a respective processor as described herein which configures and directs the processor to perform the desired functions and processes by executing the instructions encoded in the medium. It should be noted that non-transitory "computer-readable medium" as described herein may include, without limitation, any suitable volatile or non-volatile memory including random access memory (RAM) and various types thereof, read-only memory (ROM) and various types thereof, USB flash memory, and magnetic or optical data storage devices (e.g. internal/external hard disks, floppy discs, magnetic tape CD-ROM, DVD-ROM, optical disk, ZIP™ drive, Blu-ray disk, and others), which may be written to and/or read by a processor operably connected to the medium.

Aspects of the present invention may be implemented in software, hardware, firmware, or combinations thereof. The computer programs described herein are not limited to any particular embodiment, and may be implemented in an operating system, application program, foreground or background process, driver, or any combination thereof, executing on a single computer or server processor or multiple computer or server processors.

Processors described herein may be any central processing unit (CPU), microprocessor, micro-controller, or computational device or circuit configured for executing computer program instructions (e.g. code). Various processors may be embodied in computer and/or server hardware of any suitable type (e.g. desktop, laptop, notebook, tablets, cellular phones, etc.) and may include all the usual ancillary components necessary to form a functional data processing device including without limitation a bus, software and data storage such as volatile and non-volatile memory, input/output devices, graphical user interfaces (GUIs), removable data storage, and wired and/or wireless communication interface devices including Wi-Fi, Bluetooth, LAN, etc.

In certain embodiments, the present invention may be embodied in the form of computer-implemented processes and apparatuses such as processor-based data processing and communication systems or computer systems for practicing those processes. The present invention may also be embodied in the form of software or computer program code embodied in a non-transitory computer-readable storage medium, which when loaded into and executed by the data processing and communications systems or computer systems, the computer program code segments configure the processor to create specific logic circuits configured for implementing the processes.

System Overview

Figure 1:
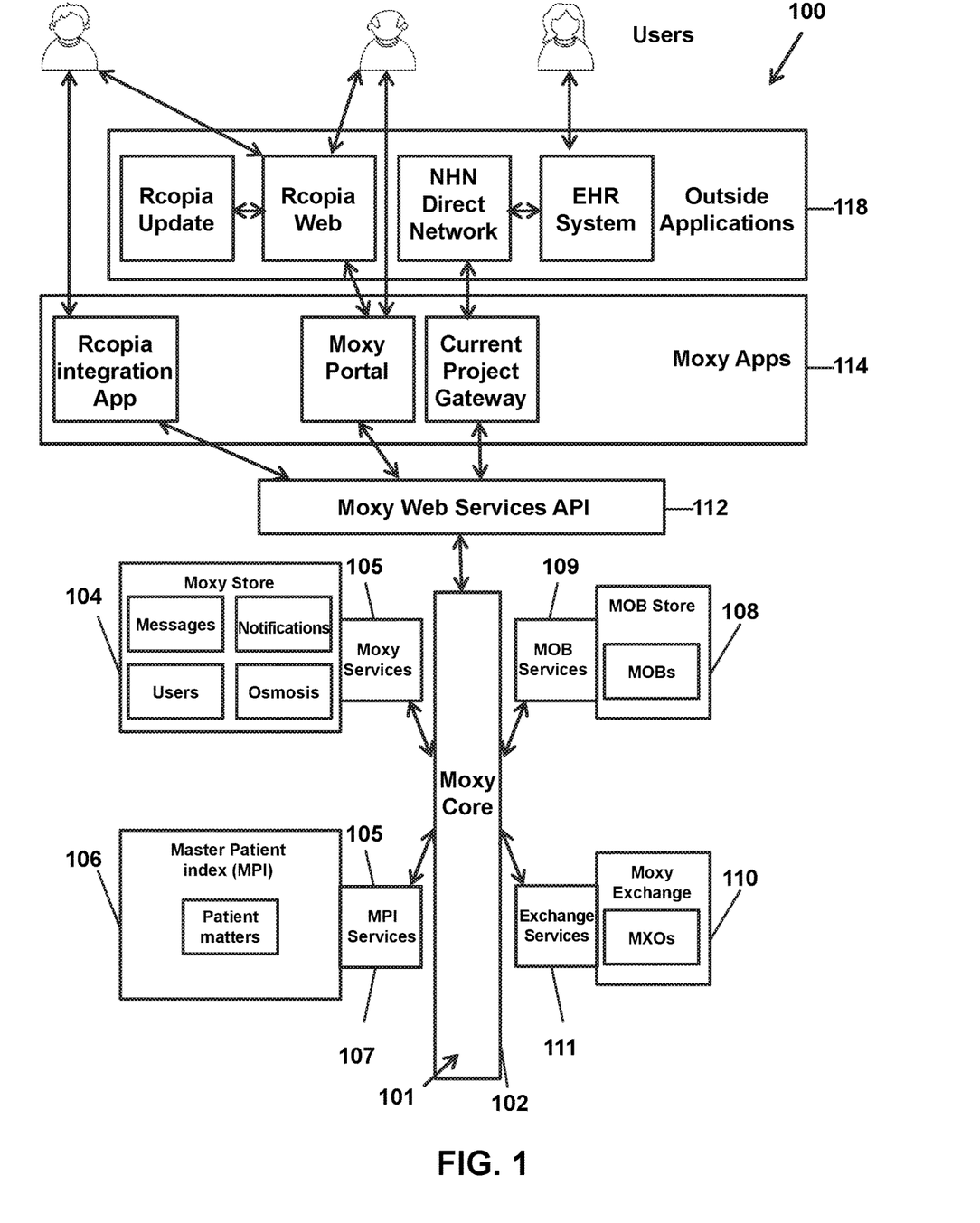
FIG. 1 is a schematic diagram of as HIE system according to one embodiment of the present invention.

A health information exchange (HIE) system 100 shown in FIG. 1 according to the present disclosure is intended as a web-based platform accessible by users via the Internet, with software applications ("apps") running that utilize the HIE Core Server 102 functions to accomplish diverse tasks, such as without limitation electronic medical records storage and retrieval in a multitude of tile formats, a full-featured secure messaging system, and others. In one embodiment, the HIE system may be Moxy™ by DrFirst® of Rockville, Md. The terms HIE and Moxy may be used interchangeably herein to refer to the HIE system 100 and associated services or components. In one embodiment, apps may use the HIE API 112 (Moxy Web Services API—application program interface) to manipulate medical data in the form of Medical Objects (MOBs), which are generic deconstructed non-descript data records not characterized by any particular known file type or format (e.g. Word, PDF, JPEG, Excel, HL7, etc.) as further described herein. Each MOB represents an atomic data piece or atomic group of data pieces created for transactional or historical reasons. Thus, MOBs may also be referred to as transaction objects. MOBs may be considered as data containers which hold attributes, properties, and the actual medical data containers (Mobbits). The attributes, properties, and Mobbit(s) are extracted by deconstructing a source medical data file of a known type. MOBs and other data record objects are generally considered not to have a known definable software program related file type. MOBs are in turn defined by extensible data schemas called Medical Object Definitions (MODs). Medical data can be converted or manipulated into different electronic file formats using Moxy Exchange Definitions (MXDs), which are also extensible.

It will be appreciated that an "object" in computer science is a term of art used to describe a record comprised of data combined with the procedures and functions that manipulate the record. All objects belong to a class. Each object belonging to a class will generally have the same fields ("attributes") and the same methods; the methods being the procedures, functions, or routines used then to manipulate the object. In the present disclosure, the data record created herein created by the HIE system 100 is referred to as Medical Object (MOB) to clarify the context and class of this type of data record.

In one embodiment, the HIE system 100 may be an open-source site containing a full Java SDK, directories of definitions and tools, and full API documentation so that outside developers may create and integrate their own apps and tools into the system.

Referring to FIG. 1, the HIE system 100 includes the HIE Core 101 ("Moxy Core") which may be comprised of an HIE Core Server 102 and HIE Core Module 103 which is a software engine or application running, on the Core Server containing instructions that directs and coordinates the overall operation of the HIE system and forms communication interfaces with external users of the system and between various components of the system. The Core Module 103 is stored on non-transitory computer readable medium accessible to the HIE Core Server 102. In some embodiments, the HIE system 100 may further include a variety of additional ancillary task specific software engines or modules (e.g. "services") stored on non-transitory computer-readable medium accessible to HIE Core Server 102 which when executed by the server configures the HIE system to perform a multitude of tasks associated with health information exchange, and in some embodiments enabling communications between users and the HIE system and between users themselves (e.g. message sending, etc.) through the HIE system. These software modules utilize databases accessible to the HIE Core Server 102 for storage, organization, and retrieval of a variety of data including MOBs, file conversion algorithms, patient profiles, etc., as further described herein.

Figure 2:
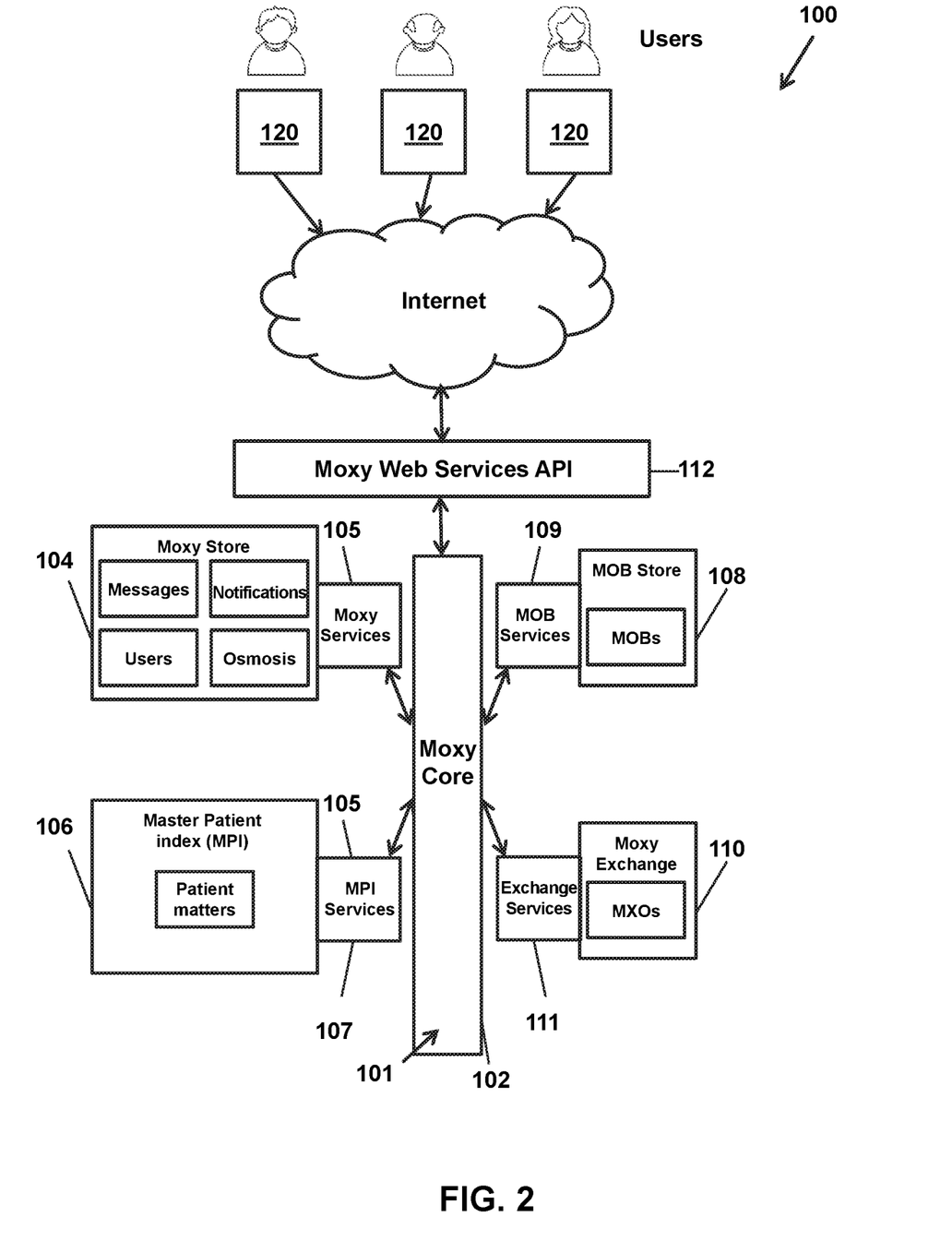
FIG. 2 is a schematic diagram of FIG. 1 showing access and communication between users and the HIE system through the Internet.

In one embodiment with reference to FIGS. 1 and 2, the task specific software modules (services) running on system 100 may include Moxy Store Services 105 with associated Moxy Store Database 104, Master Patient Index (MPI) Services 107 with associated MPI Database 106, MOB Services 109 with associated MOB Store Database 108, and HIE Data Exchange Services 111 (which may also be referred to as Moxy Exchange or Moxy Exchange Services 111 herein) with associated Moxy Exchange Database 110. These Services of the HIE system 100 are in operable communication with each other via the HIE Core Server 102 which may include a bus and wired and/or wireless communication links to the HIE system Services. In some embodiments, one or more of the components shown in FIG. 1 may be remotely located and are accessible to HIE Core Server 102 via wired or wireless data communication links including the Internet. In various embodiments, one or more of the Services 105, 107, 109, and 111 may have additional dedicated servers and the software modules may be implemented on those dedicated servers in lieu of on HIE Core Server 102. Accordingly, the invention is not limited by any of the foregoing system configurations.

Referring to FIGS. 1 and 2, the HIE API 112 includes communication protocols configured to allow a plurality of different user (source) software programs such as outside applications 118 to communicate with and use the software modules or services of the HIE system 100 to store, organize, and retrieve/exchange patient medical records. Each outside user may access the HIE system 100 through a suitably configured individual access terminal 120 shown in FIG. 2, which generally may be any type of processor-based computer device (e.g. desktop computer, laptop, notebook, tablet, cellular phone, etc.). Terminals 120 run the outside applications 118 that provide a communications interface with the HIE system and include processors, memory, input/output devices, communication interfaces, and other usual appurtenances. In one embodiment, the user access terminals 120 may be in operable communication with HIE system 100 directly through the Internet as shown in FIG. 2.

In one non-limiting example shown in FIG. 1, for instance, a health care provider associated with a care delivery organization (CDO) may communicate with HIE system 100 through API 112 via their own EHR (electronic health records) system as part of the Nationwide Health Information Network (NHIN). In this example, the health care provider uses the NHIN Direct Network to communicate through a Direct Project Gateway on the HIE system 100 (see Moxy Apps 114, FIG. 1). In other embodiments, in a similar manner, the health care provider may alternatively use NHIN CONNECT (software) if they have access to communicate with HIE system 100 via a CONNECT gateway (software) running on the HIE system. Consumer organizations that utilize personal health records (PHRs) may communicate with HIE system 100 in a similar manner. The NHIN (also referred to as eHealth Exchange), developed under the auspices of the U.S. Office of the National Coordinator for Health Information Technology (ONC), is a web-services based series of specifications designed to allow the secure exchange of healthcare related information. The NHIN access ports using CONNECT or the Direct Network provides authentication and verification processes to ensure that only authorized users have access to HIE system 100. The ONC issues Object Identifiers (OIDs) to CDO which permits the COO to access a trusted system. In one embodiment, HIE system 100 is an NHIN compliant system offering an authenticated secure site for the exchange and sharing of patient medication data and records.

In a further example shown in FIG. 1, users of an electronic prescription system such as without limitation Rcopia® by DrFirst® of Rockville, Md. may access HIE system 100 through an appropriately configured portal (e.g. Moxy Portal) or electronic prescription system integration application (e.g. Rcopia integration App). In this example, the electronic prescription system may include a built-in authentication process to ensure that only authorized users may access the patient information stored in HIE system 100. Accordingly, users of such an electronic prescription system with authentication protocols do not need to go through an NHIN portal and may access HIE system 100 directly via the electronic prescription system application software and portals.

In one aspect, the HIE system 100 is configured to manipulate electronic medical record files based on objects such as MOBs and receives, stores, exchanges, converts (e.g. the formats), and delivers medical information upon the system receiving an electronically submitted user request, as further described herein. HIE system 100 seeks to meet the long felt, but unmet need for an integrated web-based health platform that allows for the storage and exchange of patient records in virtually any format. Hitherto, HIEs and repositories have required system users to use only specific file formats regardless of the diversity of the medical source data (e.g. numerical data, tables, graphical or photographic images such as X-rays, photos, etc., and others). Otherwise, other users accessing the system seeking to retrieve and review the medical data on file would be unable to view the file contents. Advantageously, allowing medical information sources (e.g. hospitals, pharmacies, physician offices, labs, etc.) to add and share data using whatever format they standardly use can greatly decreases the difficulty of integration to a network and allows the problems of data conversion to be handled incrementally as recipient applications develop. For example, an X-ray could be attached to a patient record as a MOB. A health care provider, in pulling up the patient record from a master patient index (MPI) Database 106 of the HIE system 100, could see that the X-ray was taken, even if unable to see the X-ray itself initially. The MXD methods would then allow for the conversion of the X-ray data from one format (which might not be stored in the HIE system in a file format viewed by the provider) to a viewable, printable format such as HTML or .pdf, when a download is requested from the system by the provider.

Existing systems send the entire CCR (continuity of care record) or CCD (continuity of care documents) file from one practitioner to another. The HIE system 100 platform, however, advantageously removes the need for middleware to translate standards from one hospital or health care system to another. Individual hospitals can convert individual file records into readable or viewable documents for their specific system via HIE system 100, without concerns about presentation or translation problems. This information can then be shared with other healthcare providers, who can translate the information to best fit the needs of their own system. The creation of an entire platform would then advantageously allow providers to develop applications best suited to their practice and particular needs, stemming from a loosely-integrated patient record, rather than requiring institutions or vendors to conform before they could make any use of shared patient electronic medical data.

In one embodiment, all authorized users with access to the HIE system 100 are preferably registered in a Provider Directory and identified by for example name, date of birth, NPI (National Provider Identifier) if available, contact information, and organizational affiliations. Each user organization or institution (e.g. hospital, medical practice group, medical laboratory company, etc.) associated with the HIE system may be represented by a HIE domain in some embodiments and have a dedicated domain administrator. The domain thus represents the user organization or institution. The domain administrator creates and maintains the authorized users for the organization and has a wide array of administrative tools to monitor usage for their system integrity and the protection of patient health information (PHI). This may include reports on messaging rates, patient record view rates by user and sub-organization (e.g. departments within a hospital), and other statistics that may be of interest to the domain administrator in surveillance of their domain users of the HIE system.

Sharing information in HIE is accomplished by establishing a trust network that allows an organization to designate which other organizations, groups, and networks (i.e., which domain) may view its shared data without specific request. Such groups and networks could be comprised of doctors belonging to the same provider, doctors sharing a specific specialty, or known doctors to whom referrals are made. This facilitates sharing data on a per-patient basis for providers who may otherwise not be affiliated in any manner. Further real-world issues on data sharing are handled by override objects, which permits exceptions to be made for a given patient or record. For example, in cases where a patient wishes to exert stricter control over his/her records, the override may enable the patient to designate an object as not sharable. As another example, the patient may override the domain sharing to give specific permissions to share data with a provider who is not in the data source's trust network.

In one embodiment, the HIE system 100 includes HIE System Data Exchange Services 111 ("Moxy Exchange"), a software module that provides a framework to store, convert, and execute content from any file form into any other file form. Moxy Exchange allows for greater indexing and accessibility of records and decreases the need for file translation to meet different networks and middleware of different hospitals or institutions. HIE system 100 employs its own mechanism for storing content in any format and arrangement, labeled with metadata for ease of searching and retrieval. The stored content is contained in a searchable archive which contains patient records, such as without limitation MOB Store Database 108. Individual records are then matched to a Master Patient Index (MPI). When a patient, record is stored in the HIE system 100, patient profiles for different records with close data matches are linked, creating a continuous health record accessible by different physicians at different organizations all using the HIE system. In the event of error, users can manually unlink patients.

The Moxy Exchange Database 110 stores a plurality of file conversion algorithms each configured to convert various user source file types into a Medical Object (MOB) for storage in the MOB Store Database 108 (reference FIG. 1), and in some embodiments to further convert the MOB into a known destination file type requested by a user looking to retrieve patient medical data in a form compatible with his or her system supported medical file types, as further described herein. It is well within the ambit of those skilled in the art to write the file conversion algorithms needs for specific file type conversions without undue experimentation or further elaboration.

Operation of Health Information Exchange System

HIE system 100 in one embodiment is a data-agnostic platform—any data object can be stored regardless of format. Individual data objects tell the platform how to index them, retrieve them, convert them, and extract important elements. All data is stored as a Medical Object (MOB). The MOB comprises a MOB ID, a Medical Object Definition (MOD), a set of attributes, a set of properties, and one or more Mobbits (the actual data generated by the user's source system which has been extracted in a raw unformatted form not associated with any particular file type).

Figure 3:
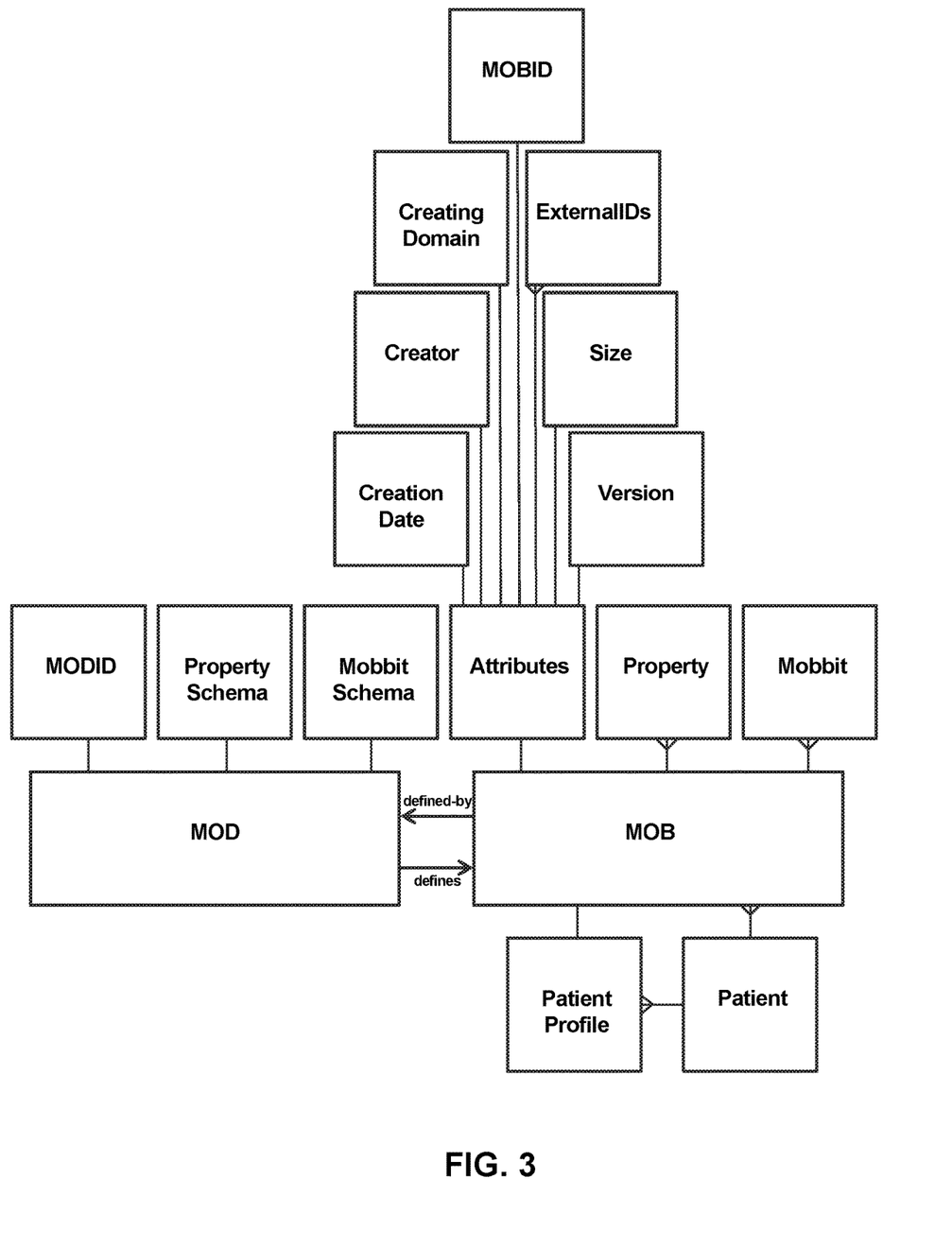
FIG. 3 is a schematic diagram showing the structure of a data record in the form of an object such as a Medical Object (MOB).

FIG. 3 depicts the component parts of a MOB with its associated MOD. As shown, the attributes of MOB which are extracted from the source medical data file may include creation date, creator, creating domain, MOBID, external IDs, size version, and others.

The Medical Object Definition (MOD) defines the structure of the MOB and contains no data itself. The MOD comprises a MOD ID (the MOD unique identifier), a property schema, and a Mobbit schema. The property schema defines the properties a MOB implementing the MOD can have in the same fashion that an XML schema (XSD) defines the permitted content of an XML document, and includes property names, value type and format, optionality, and indexability. Accordingly, the property schema contains an explicit list of properties to index the MOB implementing the MOD on. The Mobbit schema defines the Mobbits that a MOB implementing the MOD can have, including the data type, optionality, and relationship to the parent MOB. The MOD may also include a visibility attribute. The visibility attribute may determine the visibility of the MOB with respect to the domain of the MOB. For example, the value of the visibility attribute may determine whether objects (MOBs) generated for the MOD are visible to members of the domain associated with the MOB, members of domains in a trust network with the domain associated with the MOB, or any user. In some implementations, the visibility of a MOB may be overridden by an override object.

MOB properties are used for identifying different record attributes when searching or filtering records. Any MOB that contains patient data must use a MOD which contains a Patient Profile as one of its properties. A patient profile comprises patient identifying data such as without limitation name, DOB, SSN, address, and phone. Patient profiles are matched together in the MPI to a single Master Patient ID, which is used to link records on the same patient originating from different sources. Each MOB can have at most one patient profile.

A "Mobbit" is the actual data created by the user's source system. A Mobbit comprises the following elements: a label giving its association with its parent MOB; the MIME type of its data; and its content. Content can be specified directly using XML or Base 64-encoded binary, or indirectly through a URL or MOB ID.

In one embodiment, HIE system 100 is configured to convert all user patient medical data downloaded from the original source file type submitted by a user (e.g. Word, PDF, JPEG, HL7, etc.) into a deconstructed data file in the form of a Medical Object (MOB) discussed above. The MOB stored in the MOB Store Database 108 is a data record in a format which does not resemble the original source file type. FIG. 3 shows a MOB, which may generally include without limitation a MOB ID, a Medical Object Definition (MOD), a set of attributes, a set of properties, one or more Mobbits (the actual data generated by the source system), etc. During the file conversion process of the source medical data file to a MOB, the HIE system 100 therefore essentially deconstructs/disassembles the source file submitted in a known source file format/type (e.g. Word, PDF, JPEG, etc.) into a plurality of the source file's constituent parts including the actual medical data itself (Mobbit). Each MOB has an associated MOD.

A basic non-limiting, example of MOB functionality and characteristic is that of a chest X-ray series. The X-rays and all associated medical reports/information represent a transaction. The one or more documents included in the transaction that may be downloaded and stored in HIE system 100 may include: a. patient identifying data; b. technologist's notes (text); c. radiologist's interpretation (text); and d. actual X-ray-images, each labeled, e.g. PA, AP, recumbent, etc. (DICOM images). The MOB created for these documents by HIE system 100 may have a MOD (see FIG. 3) such as "Chest X-ray 1.0". The reports and images are stored in the Chest X-ray 1.0 MOB as Mobbits with suitable labels. A patient profile may be created from the patient data and added to the MOB properties. The MOB properties may also include additional useful search data including procedure code for the chest X-ray series, diagnostic code for indication, number of images taken, whether radiologist found any abnormality, and others.

If the health care provider wanted to review the results of the X-ray, he or she would search for the X-ray series using patient data, filtering by any other properties, and read the reports. The reports could be rendered into a PDF using the System Data Exchange Services 111 (Moxy Exchange) for printing. If the provider's app has the capability of viewing DICOM images, he or she could view them as well. And, if Moxy Exchange Service 111 had a definition that allowed the reports to be extracted into a format the physician's EMR system could read, he or she could import it directly.

In some implementations, the HIE system may include one or more override objects. An override object describes an explicit affirmation or denial of access to a particular medical object. It can be used with a MOB or a Mobbit, The override object identifies the object (MOB or Mobbit) the override applies to and identifies whether access is allowed or denied. The override object may specify a domain that is allowed or denied access to the object the override applies to. The override object may specify a user within a domain that is allowed or denied access to the object the override applies to. The override object may specify whether the override was explicitly requested by the patient.

HIE System Data Exchange Services ("Moxy Exchange Services")

HIE System Data Exchange Services 111 ("Moxy Exchange") establishes a framework allowing for the conversion and export of documents for different formats or content to communicate with one another. In one embodiment, the Moxy Exchange includes file conversion algorithms operable to implement the file conversions for storage and retrieval of medical data. Referring to FIGS. 1 and 2, the framework is based on, without limitation:

Moxy File Exchange Definitions (MXDs): methods for converting data from one format to another, whether MOB, data file, or display format.

Moxy File Exchange Protocols (MXPs): methods for sending data to a particular external application.

Moxy File Data Formats (MDFs): named source or destinations formats for MXDs and MXPs which includes MODs (Medical Object Definitions) and file formats (e.g., HL7, XML).

Moxy File Exchange Registry: a service for storing and looking up MXDs, MXPs, and MDFs.

Dedicated Moxy apps 114 running either on HIE Core Server 102 or alternatively on the user computer device system terminals 120 can use Moxy Exchange to: Import data from a file into a MOB; Extract MOB data into another MOB; Extract MOB data into a file for export to an outside application; Convert MOB or file data into a displayable format (e.g. HTML, PDF); Convert one file into another file; Convert a file with a given extension to a MOB or other file; Convert a MOB which has a specific property into another MOB or file.

One of the powerful applications of the MXDs is the ability to pull information from multiple recent records. For example, Moxy Exchange's ability to extract could be used in conjunction with electronic prescription software. The MXD would extract information from the patient record(s) located on Moxy (HIE system 100), to identify drugs other health care providers have prescribed. The provider could then be presented with a list of records or a list of the drugs, along with pertinent drug information data as long as the system pulled the information from as drug list to identify certain conflicting drugs, there would be no need to give the provider access to the entire record.

MXDs tell Moxy how to convert data from one format to another, whether MOB, data file, or display format. The MXD set is extensible, allowing new formats and methods to be incorporated ad lib without requiring upgrades to the Moxy service. The Moxy Data Format (MDF) is a source or destination format for converting or extracting data. All MODs are automatically MDFs. MDFs can refer to generic objects, e.g. files whose extension is ".hl7" or specific objects, e.g. "HL7ADTA08 file produced by Worthington Hospital." An MDF in an MXD or MXP can be any of the following: A user-defined file format and implementation; a MOD; any the with a given MIME type; any file with a given extension; and any MOB which contains the given MOD property.

In one embodiment, the MXDs contain file conversion algorithms including both file-to-object conversion algorithms to deconstruct/disassemble known source file formats/types (e.g. Word, PDF, JPEG, HL7, etc.) of medical data into a data record or "object" such as a MOB (Medical Object) during a source medical file download process to HIE system 100, and also object-to-file algorithms to reconstruct/reassemble MOBs back into a destination file type during a medical file upload process to a user or requestor of patient medical data, as further described herein. The file-to-object conversion algorithms deconstruct/disassemble the source file format and extract pertinent file information/data embedded in the source file (i.e. component parts) including file properties, attributes, and actual medical data (e.g. X-ray, lab results, etc.). This conversion algorithms further reorganizes and saves this information/data into the structure of the MOB shown in FIG. 3; the MOB having a different file information/data organizational structure representing the original source file information/data than the original source file, but generally retaining the same information/data without the source file format/type (e.g. Word, PDF, JPEG, HL7, etc.). The conversion process from source file to MOB also adds the MOD (medical object definition) to the MOB, as further described herein.

During the process of converting a MOB back into a requested destination file format/type, the object-to-file conversion algorithm essentially extracts the file information back out from the MOB and reconstructs/reassembles the information into a different organizational structure (than the MOB) having the requested destination tile format/type (e.g. Word, PDF, JPEG, HL7, etc.) for a requestor to view the medical data on their computer system or electronic device. The original source and requested destination file formats/types of the medical data file may be the same or different. Even where the source and destination file formats/types may be the same (e.g. same organization downloading and uploading the same medical file to HIE system 100), the HIE system 100 still converts all downloaded medical data files into a universal MOB to ensure complete data capture and integrity of the data, as already described herein.

In one embodiment, Moxy Exchange Services 111 supports the concept of the Intermediate MDF. These are MDFs are designed to be common waypoints for data conversion which bridge the gap between the format in which the MOB exists in the HIE system 100 and a file format that is compatible with acceptable formats on the user or information requestor's system. For example, a user's application wants to import the same data from two different HL7 formats (HL7-a and HL7-B) and render the extracted data into HTML for viewing, and PDF for printing. Instead of creating four MXDs to convert each HL7 file to each destination format, the Moxy Exchange performs the following steps:

1. Create an XML format to contain the common HL7 data, call this XML-I.
2. Create an MDF for that XML format, and label it as intermediate.
3. Create an MXD to convert HL7-A to XML-I.
4. Create an MXD to convert HL7-B to XML-I.
5. Create an MXD to convert XML-I to HTML.
6. Create an MXD to convert XML-I to PDF.

Advantageously, the foregoing creation and use of an Intermediate MDF by Moxy Exchange makes the files conversion more efficient. Furthermore, this approach makes future conversions simpler. For instance, if later a user wanted to convert the HL7 to a CSV file, that user can just write a single XML-I to CSV converter routine.

Figure 4:
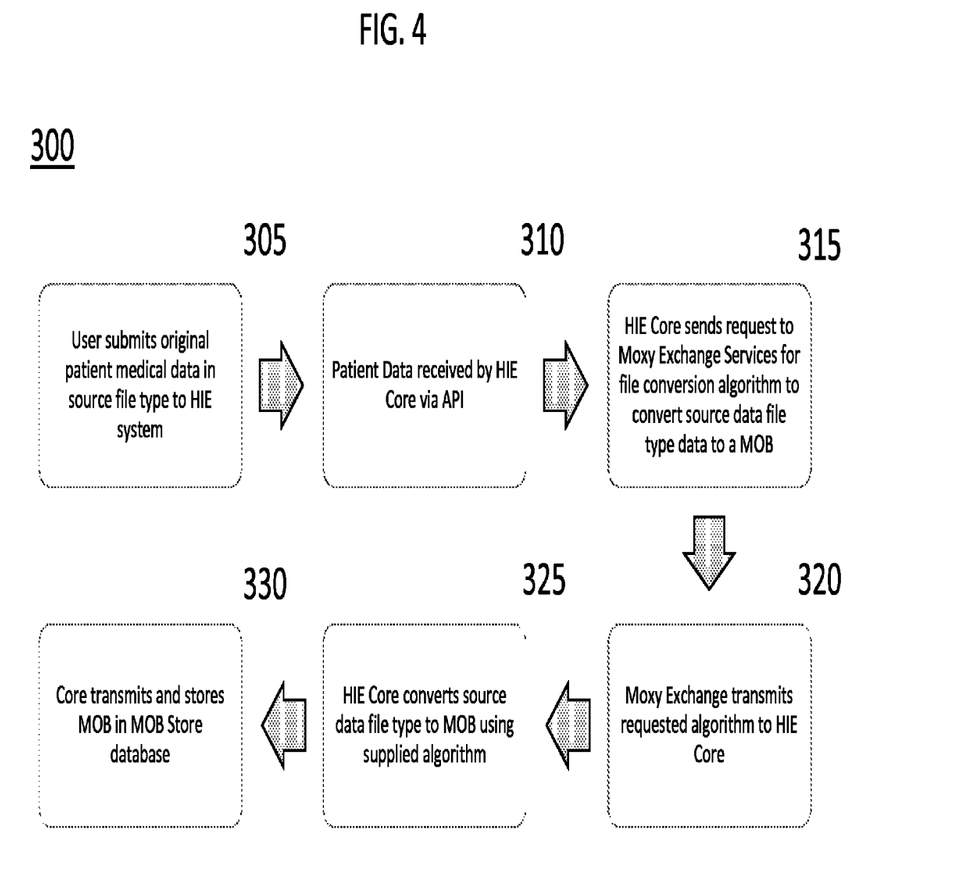
FIG. 4 is a flowchart showing an exemplary method for storing patient medical data in the HIE system of FIG. 1.

An exemplary method or process for storing patient medical records or data will now be summarized with primary reference to FIG. 4, and additional reference to FIGS. 1 and 2. In one embodiment, the HIE system 100 may operate to convert all downloaded patient medical data files regardless of source from the native source file format into a generic file format for storage and later retrieval from the system.

In step 305, the process 300 for storing medical data begins with a first user (submitter) accessing and submitting patient medical data in a medical data file (source file) through their terminal 120 to HIE system 100. In various embodiments, the medical data source file may include for example an X-ray, lab results, MM results, CCD, CCR, etc. The medical data source file may therefore be in the form of a known file type or format such as Microsoft Word (.docx), PDF (.pdf), JPEG, MP3, and others. The source file submission may preferably include at least patient demographic information (patient ID) along with the medical data so that the WE system 100 may properly associate the medical data with the given patient. The user may use any of the communication pathways shown in FIG. 1 for submitting the medical data source file to HIE system 100, or other appropriate pathways to allow the user's terminal 120 to communicate with the HIE Core Server 102 via the HIE API 112 (Moxy Web Services API). In one embodiment, the source file is submitted via the Internet.

The downloaded medical data source file is then received by HIE Core Server 102 (step 310). Next, the HIE Core 101, with HIE Core Server 102 executing the HIE Core Module 103 software program, automatically identifies the source file type and sends a request to Moxy Exchange Services 111 (HIE System Data Exchange Services 111) to provide a suitable file-to-object conversion algorithm to convert the native source file type into a Medical Object (MOB) format (see FIG. 3) based on source file type (step 315). As noted herein, the Moxy Exchange Database 110 (see FIG. 1) contains a plurality of different file conversion algorithms which are stored as MXDs in Database 110. In step 320, the Moxy Exchange Services 111 retrieves and transmits the proper algorithm requested to the HIE Core Server 102. The HIE Core Server 102 executes a conversion routine or application using the supplied conversion algorithm to convert the medical data source file type into a MOB (step 325). The MOB does not retain the original source file type, and has no specific files type but is merely an assemblage of attributes and core raw medical data (Mobbit) as shown in FIG. 3. Finally, the HIE Core Server 102 transmits and stores the MOB in the MOB Store Database 108 (step 330) which holds a plurality of MOBs. The stored MOB generic file may include patient identifying demographic information to link the file to a particular patient, as well as other tags or metadata useful for retrieving the appropriate medical data file later (see also FIG. 3). This foregoing process is repeated each time a user downloads a patient medical data source file to the HIE system 100, which in turn populates MOB Store Database 108 with MOBs for a plurality of patients.

It should be noted that in one embodiment, the actual patient MOBs (e.g. X-rays, MRIs, lab results, CCD, CCR, etc.) may be stored in the MOB Store Database 108 but the associated medical record to which the generic medical file may have been attached when submitted to HIE system 100 for storage may be stored in the separate MPI Database 106 (see also FIG. 1). The MPI Database allows a health care provider to search this database through the HIE Core 101 for all medical records associated with a specific patient, identify an MOB of interest, and then initiate a download request to view that MOB in the manner described above.

The MPI contains patient profiles categorized by each patient which may list all associated MOBs stored in the HIE system 100 for each patient. This later facilitates the filling subsequent user download requests to retrieve and display patient specific medical data from the HIE system. If a patient profile does not already exist in the MPI when a medical record and associated MOB is submitted, the HIE Core 101 may automatically create a new patient profile which is stored in the MPI to facilitate storage and later retrieval of the medical data (MOB) being submitted by the user. If a patient profile for the given patient exists in the MPI, the MPI Services 107 merely adds the submittal of a new MOB to the existing patient profile in the MPI.

Figure 5:
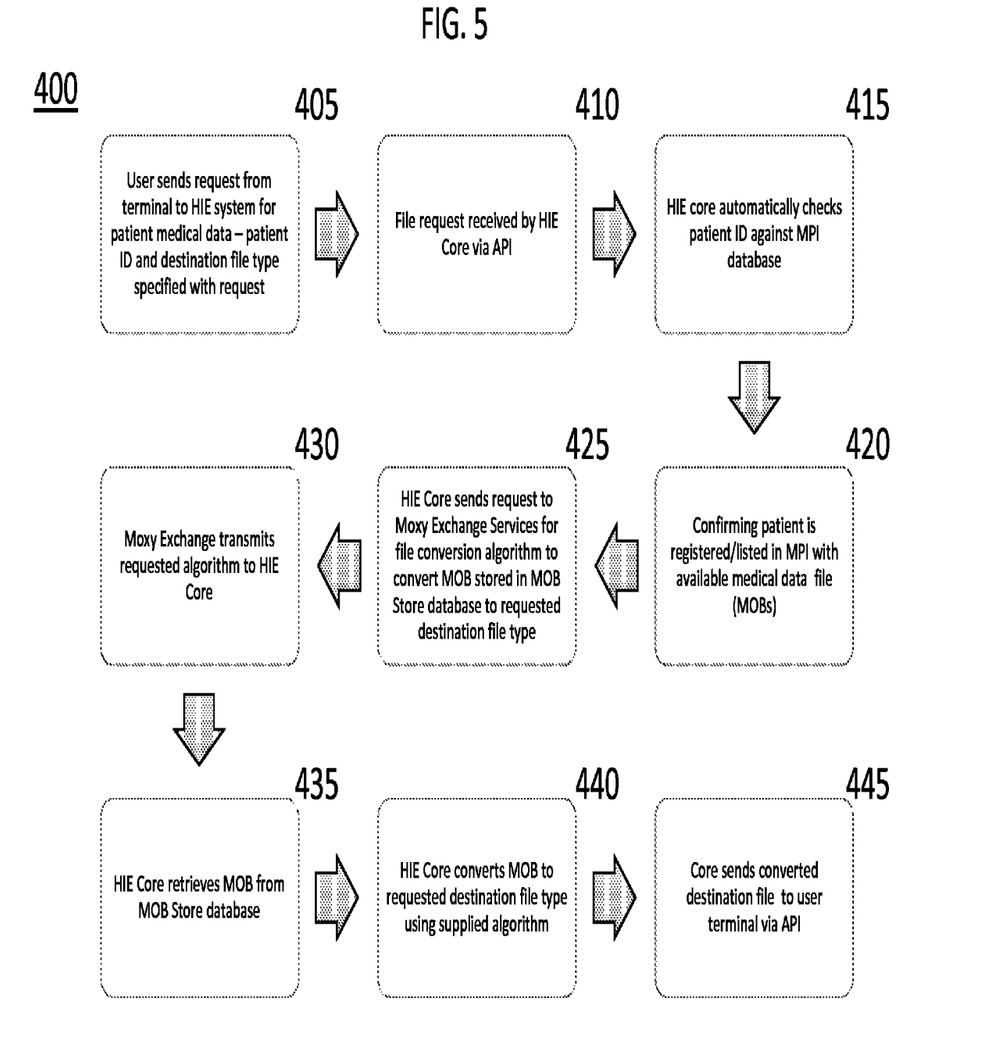
FIG. 5 is a flowchart showing an exemplary method for retrieving patient medical data from the HIE system of FIG. 1.

Referring now to FIG. 5, an exemplary method for retrieving patient medical data from HIE system 100 will now be summarized, with additional reference to FIGS. 1 and 2. In this present process, the HIE system is assumed to have been already populated with patient specific medical data (MOBs) uploaded by users (e.g. health care providers, labs, hospitals, etc.) in the manner described in the foregoing process of FIG. 4.

The method or process 400 begins with a second user (requestor) sending a request via their access terminal 120 to the HIE system 100 for medical data (e.g. X-rays, labs, etc.) for a specific patient (step 405). In one embodiment, the request includes at least two types of information—(1) patient identifying demographic information (e.g. "patient ID") and (2) the specific medical data file type (destination file type) requested by the user (e.g. HTML, .pdf, etc.) which is supported by the user's data processing system and/or organization. The destination file type may be selected by the user in a GUI such as via drop down box listing all available download file types supported by HIE system 100, direct input, or other method for selecting the file type. The supported download file types will correspond to the conversion algorithms stored in Moxy exchange Database 110 of the HIE system and accessible to the Moxy core 102 (see also FIG. 1), as described herein. Since initial access to the HIE system 100 by the second user or requestor is controlled via an authentication process, the HIE system already knows the identity of the requestor at the time the medical data request is submitted.

In some embodiments, the HIE system 100 may be configured to automatically identify the supported file types or preferences associated with the second user or requestor's organization or practice group without the user having to manually select and identify the desired medical data destination file type. Since access to the HIE system 100 in some preferred embodiments is through a user authentication process, the file types supported by the user's data processing system may be stored by the HIE Core 101 in any database accessible the HIE system. The database may therefore contain a record for each authorized system user and/or organization and their supported file types (e.g. lookup table, etc.) to ensure that the destination file type is converted into a form that can be viewed by the user when delivered by the HIE system 100. The HIE system 100 may therefore be configured and programmed to automatically look up and retrieve the supported file types associated with the requestor's organization when the request is received by HIE Core 101 (discussed below). The preferred destination file type is then automatically appended to user's request with the patient ID for further processing of the medical data request as further described below. In this embodiments, therefore, the second user or requestor merely identifies the patient and medical data requested in the request submitted to the HIE system 100 via their user terminal 120 without the need to With continuing reference now to FIGS. 1, 2, and 5, the process continues in step 410 with the medical data request being received by HIE Core 101 via the Moxy Web Services API 112. The HIE Core 101, with HIE Core Server 102 executing the HIE Core Module 103 software, then automatically checks the patient ID against the MPI (Master Patient Index) via MPI Services 107 to confirm that a patient profile exists in the MPI Database (step 415). If a patient profile for the given patient exists in the MPI, the MPI Services 107 communicates a confirmation back to the HIE Core 101 signaling that there is available medical data stored in the MOB Store Database 108 for that patient (step 420). If a patient profile does not exist, meaning that there is no medical data of record in HIE system 100 for the patient requested, a message may be returned to the user requestor via terminal 120 to that effect.

After HIE Core 101 receives the confirmation, the process continues wherein the HIE system automatically identifies the destination file type requested for download in the second user's request. Unlike the MOB, the destination file type will be a known and recognizable file format such as Word, PDF, JPEG, HTML, etc. which will allow the requestor (second user) to view the medical data. The HIE Core 101 then sends a request to Moxy Exchange Services 111 to provide a suitable object-to-file conversion algorithm to convert the requested medical data (MOB format) stored in the MOB Store Database 108 (via the process shown in FIG. 4) into the requested destination file type (step 425). As noted herein, the Moxy Exchange Database 110 (see FIG. 1) contains to plurality of different file conversion algorithms.

In step 430, the Moxy Exchange Services 111 automatically retrieves and transmits the proper algorithm (i.e. generic to destination file conversion) requested to the HIE Core 101. Simultaneously, subsequently, or prior to step 430, the HIE Core 101 retrieves the requested patient medical data (MOB) from the MOB Store Database 108 which is in generic file format (step 435). Accordingly, steps 430 and 435 may be performed in any sequence or simultaneously which does not limit the invention.

Next, in step 440, the HIE Core 101 runs a conversion routine or application using the supplied conversion algorithm to convert the requested medical data from a MOB into the specific destination file type requested by the user. Finally, the HIE Core 101 sends the fully converted destination medical file back to the user terminal 120 via the API 112 (see also FIGS. 1 and 2).

It will be appreciated that the HIE system 100 may process a plurality of user medical data download requests simultaneously using the foregoing process 400 summarized in FIG. 5. By the same token, the HIE system 100 may process a plurality of medical data upload submissions simultaneously using the foregoing process 300 summarized in FIG. 4. It will further be appreciated that the medical data file download requests and upload submissions may also be processed simultaneously by the HIE Core 101.

While the embodiment of the present invention has been described with reference to the accompanying drawings, it will be understood by those skilled in the art that the present invention can be embodied in other specific forms without departing from its spirit or essential characteristics. Therefore, the foregoing embodiments and advantages are merely exemplary and are not to be construed as limiting the present invention. The present teaching can be readily applied to other types of apparatuses. The description of the foregoing embodiments is intended to be illustrative, and not to limit the scope of the claims. Many alternatives, modifications, and variations will be apparent to those skilled in the art. In the claims, means-plus-function clauses if provided are intended to cover the structures described herein as performing the recited function and also equivalent structures.

The invention claimed is:

1. A method of storing and retrieving data in a computer system having a memory and a central processing unit, the method comprising:
    configuring said memory to store a plurality of transaction definitions, each transaction definition having a property schema and one or more data container schemas, the property schema defining one or more properties to be used for searching and filtering transaction objects generated in accordance with the transaction definition;
    receiving a selection of a transaction type and a source file having a first file format from a first user;
    obtaining, from a repository of conversion definitions, a first conversion definition having rules for converting the first file format to a transaction object corresponding to the transaction type;
    adding, responsive to the receiving, a first transaction object to a searchable archive of objects, the first transaction object being generated according to the rules of the first conversion definition, the first transaction object being defined by a transaction definition corresponding to the transaction type, the first transaction object including:
        a set of properties, each property having a value extracted from the source file in accordance with a property schema for the transaction definition corresponding to the transaction type, wherein the properties in the set of properties are indexed by respective property values and the set of properties includes a first property and patient profile properties, and
        a plurality of data containers for the source file, each data container corresponding to one of the one or more data container schemas for the transaction definition that corresponds to the transaction type, the data container identifying a data type and a label identifying a relationship between the data container and the transaction object, the data container storing content of the source file extracted into the data type;
    linking the first transaction object with a master patient identifier based on the patient profile properties of the first transaction object matching patient profile properties of a second transaction object stored in the searchable archive;
    receiving a query from a second user for transactions having the transaction type and a specific value for the first property;
    using the indexed first property to determine the transaction object is responsive to the query and to present the transaction object for importing;
    receiving a request, from the second user, to import the first transaction object in a second file format;
    selecting, from the repository of conversion definitions, a second conversion definition having rules for converting the transaction object to the second file format;
    converting the transaction object to a destination file having the second file format according to the rules of the second conversion definition; and
    providing the destination file to the second user.

2. A data storage and retrieval system for a computer, comprising:

a repository of transaction definitions, each transaction definition representing a transaction and including:
  a property schema, defining one or more properties to be used for searching and filtering transaction objects generated in accordance with the transaction definition, and
  data container schemas for data containers included in transaction objects defined by the transaction definition;
a searchable archive of transaction objects, each transaction object being defined by one of the transaction definitions and including:
  a set of properties, each property having a value extracted from a source file and indexed, and
  a plurality of data containers, each data container corresponding to one of the data container schemas for the transaction definition and identifying a data type and including content of a source file related to the transaction object,
  wherein at least some transaction objects have a first property and patient profile properties included in the set of properties;
a repository of conversion definitions, each conversion definition corresponding to a file type and configured to either:
  convert a file of the file type to a transaction object, or
  convert a transaction object to a file of the file type; and
a memory storing instructions that, when executed by the data storage and retrieval system, are configured to:
  receive, from a first user, a selection of a transaction type and at least one source file having a first file format,
  obtain, from the repository of conversion definitions, a first conversion definition having rules for converting the first file format to a transaction object corresponding to the transaction type,
  add a first transaction object to the searchable archive responsive to the receiving, the transaction object, the first transaction object being generated using the rules of the first conversion definition, the first transaction object being defined by a transaction definition corresponding to the transaction type and including:
    a set of properties extracted from the at least one source file in accordance with a property schema for the transaction definition corresponding to the transaction type, wherein the properties in the set of properties are indexed by respective property values and the set of properties includes a first property and patient profile properties, and
    a plurality of data containers generated for the at least one source file, each data container corresponding to one of the one or more data container schemas for the transaction definition that corresponds to-the transaction type, the data container identifying a data type and a label identifying a relationship between the data container and the transaction object, the data container storing content of the source file extracted into the data type,
  link the first transaction object with a master patient identifier based on the patient profile properties of the first transaction object matching patient profile properties of a second transaction object stored in the searchable archive,
  receive a query from a second user for transactions having the transaction type and a specific value for the first property,
  use the indexed first property to determine the transaction object is responsive to the query and to present the transaction object for importing,
  receive a request, from the second user, to import the first transaction object in a second file format,
  select, from the repository of conversion definitions, a second conversion definition having rules for converting the transaction object to the second file format,
  convert the transaction object to a destination file having the second file format according to the rules of the second conversion definition, and
  provide the destination file to the second user.

3. The method of claim 1, wherein the transaction definition has a visibility attribute inherited by the transaction object, the visibility attribute determining visibility of the transaction object with respect to a domain attribute of the transaction object and the method further includes:
  receiving an override object for the transaction object, wherein the override object overrides the visibility attribute.

4. The method of claim 1, wherein a data container schema defines a data type, an optionality, and a relationship to the transaction object.

5. The method of claim 1, further comprising receiving a plurality of source data files to associate with the transaction type, each source data file having a respective file type, wherein the transaction object generated in response to receiving the transaction type includes a respective data container for each of the plurality of source data files.

6. The method of claim 1, further comprising:
  using the set of properties to identify the transaction object prior to receiving the request from the second user to receive the transaction object in the second file format.

7. The method of claim 1, further comprising:
  associating a first domain with the transaction object;
  receiving a request for the transaction object from a user associated with a second domain;
  determining whether the second domain is in a trust network with the first domain; and
  preventing the user from accessing the transaction object when the second domain is not in a trust network with the first domain.

8. The method of claim 7, further comprising:
  determining that the transaction object has a visibility attribute that indicates the transaction object is visible to members of the trust network; and
  enabling the second user to access the transaction object responsive to determining that the transaction object has the visibility attribute and the second domain is in the trust network with the first domain.

9. The method of claim 1, the method further comprising:
  configuring the memory to store a plurality of conversion definitions, each conversion definition including:
    a source data definition,
    a destination data definition, and
    rules for transforming data in the source data definition to data in the destination data definition,
  wherein each of the plurality of transaction definitions and the first file format are examples of data definitions.

10. The method of claim 1, wherein the method further comprises:
  identifying, for a plurality of transaction objects, a subset of transaction objects having respective first property values that match a value in a query identifying the first property; and providing the subset of transaction objects in response to the query.

11. The method of claim 1, wherein the method further comprises:
receiving a query;
determining patient profiles that are responsive to the query; and
providing transaction objects associated with the determined patient profiles in response to the query.

12. The system of claim 2, wherein the patient profile properties comprises at least three properties selected from the group including name, date of birth, address, government issued identification number, and phone number.

13. The system of claim 12, wherein a data container schema defines a data type, an optionality, and a relationship to the transaction object.

14. The system of claim 2, wherein the instructions are further configured to:
identify, for a plurality of transaction objects, a subset of transaction objects having respective first property values that match a value in a query identifying the first property; and
provide the subset of transaction objects in response to the query.

15. The system of claim 2, wherein each transaction object is associated with a first domain as an attribute of the transaction object, wherein the first domain is part of a trust network with a second domain, and the instructions are further configured to:
facilitate sharing of data from the transaction object with users associated with the first domain or with the second domain; and
prevent sharing of data from the transaction object with users not associated with the first domain or with the second domain.

16. The system of claim 15, wherein the instructions are further configured to:
receive an access override for the transaction object, the access override denying access to the second domain; and
prevent sharing of data from the transaction object with users associated with the second domain.

17. The system of claim 2, wherein the instructions are further configured to:
receive a second source file having a second file type;
receive a selection of the transaction object; and
generate a second data container for the second source file using a conversion definition from the repository of conversion definitions that corresponds to the second file type and to the transaction type, the second data container being associated with the transaction object.

18. The system of claim 2, wherein the transaction definition has a visibility attribute inherited by the transaction object, the visibility attribute determining visibility of the transaction object with respect to a domain attribute of the transaction object.

19. The system of claim 2, wherein the instructions are further configured to:
associate a first domain with the first transaction object;
receive a request for the first transaction object from a user associated with a second domain;
determine whether the second domain is in a trust network with the first domain; and
prevent the user from accessing the first transaction object when the second domain is not in a trust network with the first domain.

20. The system of claim 19, wherein the instructions are further configured to:
determine that the transaction object has a visibility attribute that indicates the transaction object is visible to members of the trust network; and
enable the second user to access the transaction object responsive to determining that the transaction object has the visibility attribute and the second domain is in the trust network with the first domain.

* * * * *